United States Patent [19]

Southgate et al.

[11] Patent Number: 4,521,337

[45] Date of Patent: Jun. 4, 1985

[54] CHEMICAL PROCESS

[75] Inventors: Robert Southgate, Warnham; Pamela Brown, Guildford, both of England

[73] Assignee: Beecham Group p.l.c., England

[21] Appl. No.: 475,247

[22] Filed: Mar. 14, 1983

[30] Foreign Application Priority Data

Mar. 16, 1982 [GB] United Kingdom ................ 8207619

[51] Int. Cl.$^3$ .......................................... C07D 498/04
[52] U.S. Cl. ................................ 534/560; 204/158 R; 204/158 HE; 544/71; 544/90
[58] Field of Search ............... 260/141 D; 544/71, 90; 204/158 R, 158 HE

[56] References Cited

U.S. PATENT DOCUMENTS 4,245,089  1/1981  Ponsford et al. .................... 544/71
4,443,599  4/1984  Smale .................................. 544/90

Primary Examiner—Richard L. Raymond
Attorney, Agent, or Firm—Jacobs & Jacobs

[57] ABSTRACT

A process for the preparation of a compound of the formulae (Ia) and/or (Ib):

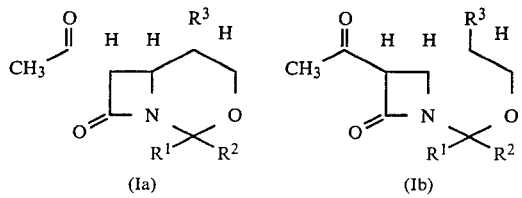

wherein $R^1$ and $R^2$ are independently substituted or unsubstituted hydrocarbon groups or are joined together so as to form a carbocyclic or heterocyclic ring, and $R^3$ is a substituted or unsubstituted hydrocarbon group; which process comprises the ring-closing cyclization of a compound of the formula (II):

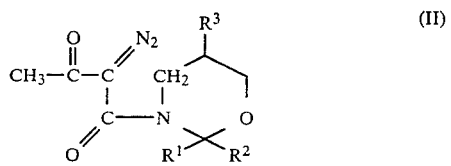

wherein $R^1$, $R^2$ and $R^3$ are as defined in relation to formulae (Ia) and (Ib).

8 Claims, No Drawings

CHEMICAL PROCESS

The present invention relates to a chemical process and to intermediates formed therefrom which are of use in the synthesis of 4-substituted 7-oxo-1-azabicyclo[3.2.0]heptene antibacterial agents.

Accordingly, this invention provides a process for the isolation of the compounds of the formulae (Ia) and/or (Ib):

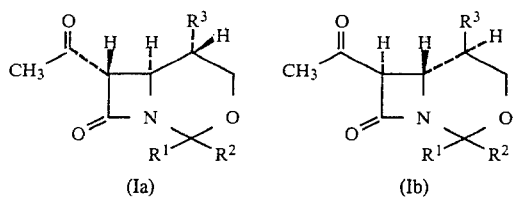

(Ia)          (Ib)

wherein $R^1$ and $R^2$ are independently substituted or unsubstituted hydrocarbon groups or are joined together so as to form a carbocyclic or heterocyclic ring, and $R^3$ is substituted or unsubstituted hydrocarbon group; which process comprises the ring-closing cyclisation of a compound of the formula (II):

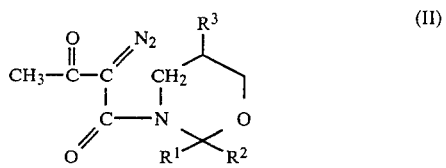

wherein $R^1$, $R^2$ and $R^3$ are as defined in relation to formulae (a) and (b).

The compound of the formula (II) has a chiral centre at the ring carbon bearing the $R^3$ group. It has been found that the cyclisation process produces predominantly a product wherein $R^3$ is in a cis-relationship to the C-6 proton. Therefore in a particularly favoured aspect of this invention, the compound of the formula (II) is optically active, so that the ring-closing cyclisation gives rise to an optically active compound. For example the compound of the formula (III) will afford the compound of the formula (Ia):

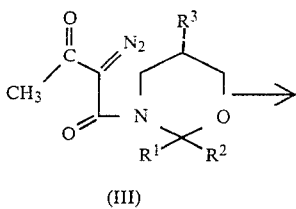

(III)

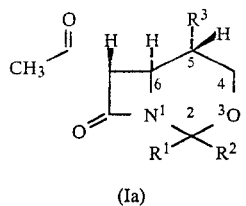

(Ia)

wherein $R^1$, $R^2$ and $R^3$ are as hereinbefore defined.

Suitably $R^1$ and $R^2$ are the same or different unsubstituted hydrocarbon groups of up to 20 carbon atoms. Preferably $R^1$ is selected from $C_{1-6}$ alkyl such as methyl, ethyl, propyl and butyl. Preferably $R^2$ is selected from $C_{1-6}$ alkyl such as methyl, ethyl, propyl and butyl.

In an alternative aspect $R^1$ and $R^2$ are joined so as to form together with the carbon atom to which they are attached a substituted or unsubstituted carbocyclic or heterocyclic ring, where for example the carbocyclic or heterocyclic ring contains from 3 to 8 ring atoms. Suitably in a heterocyclic ring, one, two or three heteroatoms are present selected from oxygen, nitrogen and sulphur.

Suitable substituents for $R^1$ and $R^2$, either when independent or joined so as to form a ring, include $C_{1-6}$ alkyl, hydroxy, bromine, chlorine, fluorine, carboxylic acid or salt or ester thereof, azido, tetrazolyl, alkanoyl, alkanoyloxy, aroyloxy, aroyl, aralkanoyloxy, aroxy, amino, protected amino, nitro, $C_{1-6}$ alkoxy, $C_{1-6}$ alkyl, aryl, $C_{1-6}$ alkylthio and arylthio.

Suitably $R^1$ and $R^2$ together with the carbon atom to which they are attached form a spiro- cyclohexane or cyclopentane ring.

Suitably $R^3$ is substituted or unsubstituted: $C_{1-6}$ alkyl such as methyl, ethyl, propyl and butyl, $C_{2-10}$ alkenyl, $C_{2-10}$ alkynyl, $C_{3-6}$ cycloalkyl, $C_{3-6}$ cycloalkyl($C_{1-6}$)alkyl, aryl such as phenyl, aryl($C_{1-6}$)alkyl such as benzyl, aryl($C_{2-6}$)alkenyl, aryl($C_{2-6}$)alkynyl, heteroaryl, heterocyclyl, heteroaryl($C_{1-6}$)alkyl and heterocyclyl($C_{1-6}$)alkyl; wherein the hetero atom or atoms in the heteroaryl and heterocyclyl rings (of up to 10 ring atoms) are selected from 1 to 4 oxygen, nitrogen or sulphur atoms.

Suitable substituents for the group $R^3$ include amino, mono-, di- and trialkylamino, hydroxyl, alkoxyl, mercapto, alkylthio, arylthio such as phenylthio, sulfamoyl, amidino, guanidino, nitro, chloro, bromo, fluoro, cyano and carboxy.

Preferably in the process of this invention $R^3$ is $C_{1-6}$ alkyl such as methyl, ethyl, n-propyl, isopropyl or butyl, or benzyl. Most favourably $R^3$ is methyl.

In one aspect the ring-closing cyclisation may be effected by photolysis, for example by irradiation. This may be conveniently performed utilising a 450 W Hanovia medium pressure mercury lamp with a Pyrex reaction vessel. Generally the photolysis reaction is carried out at a depressed temperature, for example −20° C. to −80° C., in an inert solvent such as diethyl ether.

In a preferred aspect the cyclisation may be effected by metal-catalysed intramolecular carbenoid insertion such as by a rhodium (II) species, for example Rhodium (II) acetate, in an organic solvent such as benzene or toluene, preferably benzene.

The isolation of the compounds of the formula (Ia) and/or (Ib) from the reaction mixture, may be performed by crystallisation and/or chromatography. Suitably chromatography may be performed on columns of silica gel eluting with halohydrocarbons such as chloroform. Crystallisation of the compounds of the formulae (Ia) and/or (Ib) may be effected from an organic solvent or a mixture of organic solvents, for example a hydrocarbon such as hexane may be used.

The compounds of the formula (II) are novel and as such form part of the present invention.

The compounds of the formula (II) may be prepared by the reaction of a compound of the formula (IV):

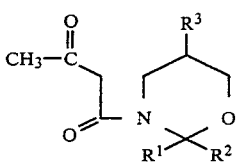

wherein $R^1$, $R^2$ and $R^3$ are as hereinbefore defined, with a diazo-transfer reagent such as methanesulphonyl azide in the presence of a tertiary base such as triethylamine. Generally the reaction is performed in an organic solvent such as benzene at an approximately ambient temperature.

The compounds of the formula (IV) may be prepared by the reaction of diketene with a compound of the formula (V):

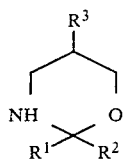

wherein $R^1$, $R^2$ and $R^3$ are as hereinbefore defined.

The compounds of the formula (V) may be prepared by adaptation of the methods of Hancock et al. J. American. Chemical Society 1944 66, p 1947. For example, according to the following Scheme:

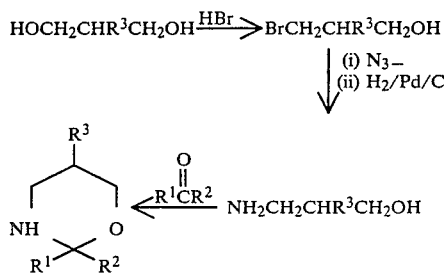

The compounds of the formulae (Ia) and/or (Ib) may be converted to 4-substituted 7-oxo-1-azabicyclo[3.2.0-]heptene-2-carboxylate in conventional manner, for example, see European Patent Application Publication Nos: 0008888 and 0010317.

Thus in another aspect the present invention provides the use of isolated compounds of formulae (Ia) and/or (Ib) in the preparation of a β-lactam containing antibacterial agent.

The following Examples illustrate the invention. In examples 4–6 inclusive, only one enantiomer is depicted for convenience.

EXAMPLE 1

3-bromo-2-methyl propan-1-ol

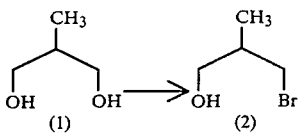

3-Bromo-2-methyl propan-1-ol was prepared according to the method of Searles et al., J. Org. Chem., 1959, 24, 1839. 2-methyl propan-1,3-diol (1), (1.78 g) (E. R. Nelson, M. Maienthal et al., J. Amer. Chem. Soc., 1957, 79, 3467) was treated with acetic acid (4 ml) and 48% hydrobromic acid (0.1 ml) and heated to reflux for 20 minutes. A solution of 45% hydrogen bromide in acetic acid (4 ml) and acetic acid (4 ml) was added to the refluxing reaction over a period of 3 h., and refluxing continued for a further 8 h. The product was concentrated under reduced pressure and treated with 48% hydrobromic acid (0.1 ml) in ethanol (7 ml). The solvents were distilled under atmospheric pressure, and the procedure repeated twice until the distillate no longer contained ethyl acetate. The residue was distilled under reduced pressure to yield 3-bromo-2-methyl propan-1-ol (2) (1.67 g); b.p. 88°–90° C. (20 mm); $\nu_{max.}$ ($CH_2Cl_2$) 3620, 3300, 2960, 1460, 1380, 1230, 1030, 980, 650, 620 cm$^{-1}$; δ ($CDCl_3$) 1.00 (3H, d, J=7 Hz, $CH_3$); 1.80–2.30 (1H, m, C(2)H); 3.50 (2H, d, J=6 Hz); 3.62 (2H, d, J=6 Hz); 5.95 (1H, br.s. $D_2O$ esch., OH).

EXAMPLE 2

3-azido-2-methyl propan-1-ol

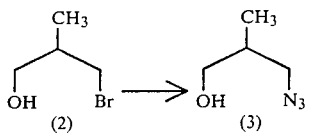

A solution of 3-bromo-2-methyl propan-1-ol (2) (12.5 g) in dry dimethyl formamide (50 ml) was treated with finely-ground sodium azide (10 g) and tetramethylguanidinium azide (2 g). The reaction mixture was stirred at 90° C. for 24 hours, adding a further portion of sodium azide (5 g) after 16 h. The reaction mixture was poured into water (75 ml), the product extracted into ethyl acetate and the organic phase washed with 3% sodium bicarbonate solution (5×25 ml). The combined aqueous extracts were back-extracted into ethyl acetate (50 ml) and the combined organic extracts dried over anhydrous magnesium sulphate. Evaporation of the solvent gave 3-azido-2-methyl propan-1-ol (3) (9.1 g) as a colourless oil which was not purified further; $\nu_{max.}$ ($CHCl_3$) 3620, 3420, 2120, 1460, 1390, 1280, 1030 cm$^{-1}$; δ (ppm, $CDCl_3$) 1.00 (3H, d, J=7 Hz, $CH_3$); 1.70–2.20 (1H, m, C(2)H); 3.10 (1H, br.s., OH), 3.40 (2H, d, J=6 Hz), 3.55 (2H, d, J=6 Hz).

EXAMPLE 3

3-amino-2-methyl propan-1-ol

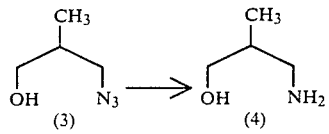

3-azido-2-methyl propan-1-ol (3) (9.85 g) was dissolved in ethanol (120 ml), treated with 10% paladium on charcoal (0.5 g) and hydrogenated at atmospheric pressure in an apparatus containing 750 ml hydrogen. The reaction was carried out for 4 hours, replacing the gas in the vessel with fresh hydrogen at hourly intervals. The reaction mixture was filtered through Kieselguhr and the solvent evaporated under reduced pressure to give 3-amino-2-methyl propan-1-ol (4) as a colourless oil which was not purified further; $\nu_{max.}$ (CH₂Cl₂) 3620, 3380, 3300 br., 1585, 1460, 1390, 1030 cm⁻¹; δ (ppm., CDCl₃) 0.90 (3H, d, J=7 Hz, CH₃); 1.46 (1H, m, C(2) H); 2.72 (2H, d, J=6 Hz, CH₂NH₂); 2.97 (2H, s, NH₂); 3.25 (1H, br. s. OH), 3.50 (2H, d, J=6 Hz, CH₂OH).

EXAMPLE 4

1-[3-Methyl-1-oxa-5-azaspiro[5.5]undecan-5-yl]butan-1,3-dione

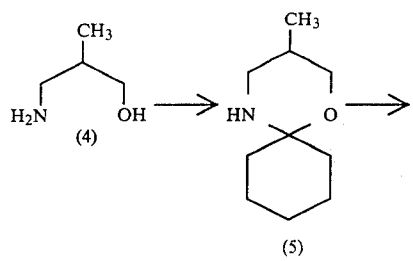

(5)

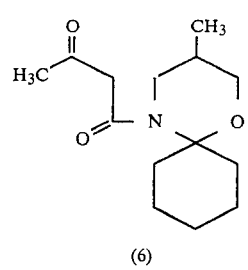

(6)

A solution of 3-amino-2-methyl propan-1-ol (4) (0.400 g) in dry benzene (10 ml) was treated with cyclohexanone (0.450 g) and heated at reflux in an apparatus with provision for water removal for 5 hours. The product was concentrated to give the crude 3-methyl-1-oxa-5-azospiro[5.5]undecane (5) as a yellow oil; ν_max. (CH₂Cl₂) 3450, 1660 (weak, Schiffs base); 1460, 1450, 1160, 1040 cm⁻¹. This material was redissolved in dry benzene (10 ml) and stirred and cooled in an ice-bath, treated with diketene (0.37 ml) and stirring continued at 0° C. for 1 h followed by room temperature for 1 h. The solvent was evaporated and the residue chromatographed on Kieselgel 60 (<230 mesh ASTM) eluting with hexane grading to 1:1 ethyl acetate/hexane, to give 1-[3-methyl-1-oxa-5-azaspiro[5.5]undecan-5-yl]butan-1,3-dione (6) (0.400 g) as a yellow oil; ν_max (CH₂Cl₂) 1725, 1640, 1450, 1410, 1550 cm⁻¹; δ (ppm, CDCl₃) 0.96 (3H, d, J=7 Hz, CH₃ CH); 1.25–2.70 (10H, m, cyclohexyl); 2.10–2.20 (1H, m, CH₃CH); 2.27 (3H, s, C(O)CH₃); 3.10 (1H, dd, J=12, 7 Hz, CHaHbN); 3.27 (1H, dd, J=11, 7 Hz, CHaHbO); 3.34 (1H, dd, J=12, 7 Hz, CHAHb N); 3.50 (2H, d, J=2.5 Hz, COCH₂CO); 3.94 (1H, dd, J=11, 7 Hz, CHaHbO).

EXAMPLE 5

1-[3-methyl-1-oxa-5-azaspiro[5.5]undecan-5-yl]-2-diazabutan-1,3-dione

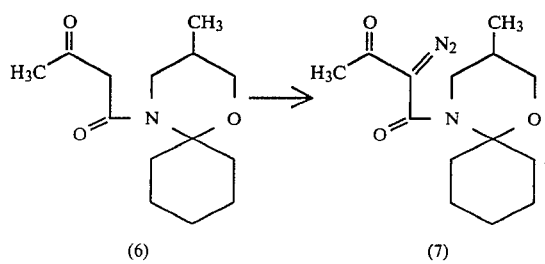

(6)                    (7)

1-[3-Methyl-1-oxa-5-azaspiro[5.5]undecan-5-yl]butan-1,3-dione (6) (9.7 g) was dissolved in dry toluene (125 ml) and cooled to 0° C. The solution was treated with triethylamine (6 g), piperidine (0.1 g) and mesyl azide (7 g) in toluene (30 ml), stirred at 0° C. for 1 hr then allowed to warm to room temperature and stirred for 40 hr. The solvent was evaporated and the residue chromatographed on Kieselgel 60 (<230 mesh ASTM) using 1:4 ethyl acetate/hexane as eluant, to give 1-[3-methyl-1-oxa-5-azaspiro[5.5]undecan-5-yl]-2-diazabutan-1,3-dione (7) (8.76 g) as a yellow oil, contaminated with mesyl azide in approximately 1:1 molar ratio ν_max (CH₂Cl₂) 2140 (mesyl azide), 2110 1660 br., 1390, 1365, 1200, 1170, 1060, 965 cm⁻¹; δ (ppm, CDCl₃); 0.95 (3H, d, J=7 Hz, CH₃CH); 1.25–2.70 (10H, m, cyclohexyl-H); 2.15–2.29 (1H, m, CH₃CH); 2.34 (3H, s, C(O)CH₃); 3.15 (1H, dd, J=12, 7 Hz, CHaHbN); 3.28–3.38 (2H, m, CHaHbN and CHaHbO); 3.93 (1H, dd, J=12, 7 Hz, CHaHbO).

EXAMPLE 6

(5'RS,6'SR,7'RS)-7'-Acetyl-5'-methylspiro[cyclohexane-1,2'-[3]oxa[1]azabicyclo[4.2.0]octane]-8'-one.

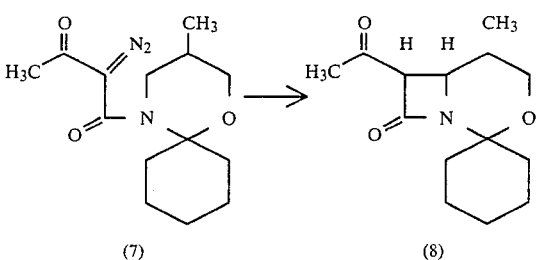

(7)                    (8)

1-[3-Methyl-1-oxa-5-azaspiro[5.5]undecan-5-yl]-2-diazobutan-1,3-dione (7) (6.13 g) was dissolved in toluene (70 ml) and added to a stirred suspension of rhodium II acetate (0.70 g) in toluene (30 ml) The reaction mixture was stirred at room temperature for 22 h followed by 2 h at 50° C. The mixture was filtered through Kieselguhr, the solvent evaporated and the residue chromatographed on Kieselgel 60 (<230 mesh ASTM) using 1:3 ethyl acetate/hexane as eluant. From the first fractions was obtained the title compound (5' RS, 6'SR, 7'RS)-7'-acetyl-5'-methylspiro[cyclohexane-1,2'-[3]oxa[1]azabicyclo[4.2.0]octane]-8'one (8) (2.902 g) as a pale yellow oil which was crystallised from hexane; m.p. 109°–110° C., ν_max. (CH₂Cl₂) 1775, 1715, 1365, 1200 cm⁻¹; δ (ppm, CDCl₃) 0.89 (3H, d, J=7 Hz, 5'-CH₃); 1.35–1.88 (10H, m, cyclohexyl-H and 5'-H); 2.20–2.28

(1H, m, cyclohexyl-H); 2.32 (3H, s, C(O)CH₃); 3.51–3.74 (3H, m, contains [3.59(1H, dd, J=2, 8 Hz, 6'-H); 3.76 (d,J=12 Hz) and 3.72 (d, J=12 Hz part of 2×ABq of 4'-H]; 3.81 (1H, d, J=2 Hz, 7'-H). Evaporation of the middle fractions gave an oil (0.441 g) containing predominantly (8) with a small amount of the 5'-epimer; (5'RS, 6'RS, 7'SR)-7'-acetyl-5-methylspiro[cyclohexane-1,2'-[3]oxa[1]azabicyclo[4.2.0]octane]-8'-one, from which (8) was obtained pure by crystallisation from hexane. The later fractions gave an oil (0.460 g) consisting of a 1:1 mixture of (8) and its 5'-epimer. The NMR spectrum of the latter showed, by difference; δ (ppm, CDCl₃); 1.14 (3H, d, J=7 Hz, 5'-CH₃ 1.35–1.92 (10H, m, cyclohexyl and 5'-H); 1.92–2.00 (1H, m, cyclohexyl); 2.32 (3H, s, C(O)CH₃); 3.56 and 3.62 (1H, 2d, J=2 Hz, 4'-H); 3.97 and 4.02 (1H, 2d, J=2 Hz, 4'-H); 4.02 (1H, d, J=2 Hz, 7'-H); 4.17 (1H, dd, J=2,5 Hz, 6'-H).

EXAMPLE 7

(i) Resolution of 3-amino-2-methyl propan-1-ol

To a solution of racemic 3-amino-2-methyl propan-1-ol (4) (3.0 g) in methyl ethyl ketone (65 ml) was added (−) N-(1-phenylethyl)-succinamic acid (7.6 g) (E. Felder, D. Pitre and S. Boveri, Helv. Chim. Acta, 1969, 52, 329) at 60° C. and the mixture stirred until dissolved. On cooling the stirred solution to ambient temperature, the desired salt was precipitated. This was filtered, washed with ether and dried in vacuo to yield 3.7 g of crystalline material. On recrystallisation from methylethyl ketone the optical rotation remained constant; $[\alpha]_D^{20} = -64.2°$ (C=1, ethanol); m.p. 112°–115° C.; Found: C, 61.59; H, 8.29; N, 8.95%, $C_{16}H_{26}N_2O_4$ requires C, 61.94; H, 8.39; N, 9.03%.

A solution of the salt in methanol was applied to strongly basic ion-exchange column (αAmberlysta A-26 resin) Elution with methanol followed by evaporation of solvent gave the optically active amino alcohol; $[\alpha]_D^{20} = +7.8°$ (C=1.7, chloroform).

In a similar manner, the (−) amino alcohol was prepared by resolution using (+) N-(1-phenylethyl)-succinamic acid.

(ii) The above resolved materials are converted to optically active compounds of the formula (8) by the method of Examples 8–11 hereinafter.

EXAMPLE 8

1-[(S)-3-Methyl-1-oxa-5-azaspiro[5.5]undecan-5-yl]butan-1,3-dione

The salt of (+)-(S)-3-amino-2-methyl propan-1-ol with (−)-N-(1-phenylethyl)-succinamic acid was prepared as described in Example 7. This gave a rotation of −67.8° (cl, ethanol).

The salt (41.0 g) was suspended in dry benzene (500 ml) treated with triethylamine (13.3 g) and cyclohexanone (14.8 g) and the mixture heated to reflux in an apparatus with provision for water removal for 5 hours. The solution was cooled to 0° C., filtered and the filtrate treated with diketene (9.6 ml) at 0° C. under an argon atmosphere and the mixture stirred at 0° C. for 1.5 hours.

The solvent was evaporated and the residue chromatographed on Kieseigel 60 (<230 mesh ASTM) eluting with hexane grading to 1:1 ethyl acetate/hexane to give the title compound (23.2 g, 70%), $[\alpha]_D^{20} = -22.1°$ (cl, chloroform).

EXAMPLE 9

1-[(S)-3-Methyl-1-oxa-5-azaspiro[5.5]undecan-5-yl]-2-diazabutan-1,3-dione

1-[(S)-3-Methyl-1-oxa-5-azaspiro[5.5]undecan-5-yl]butan-1,3-dione was converted into the title compound in 65% yield on treatment with methane sulphonyl azide under the conditions described in Example 5.

EXAMPLE 10

(5'S,6'R,7'S)-7'-Acetyl-5'-methylspiro[cyclohexane-1,2'-[3]oxa[1]azabicyclo[4.2.9]octane]-8'-one Cyclisation of 1-[(S)-3-Methyl-1-oxa-5-azaspiro[5.5]undecan-5-yl]-2-diazabutan-1,3-dione under the conditions described in Example 6 took place in 64% yield. The product was a mixture of epimers at C-5' of which 88% was the title compound. This was obtained pure by column chromatography, $[\alpha]_D^{20} = +4.5°$ (c2, chloroform).

EXAMPLE 11

(5'R,6'S,7'R)-7'-Acetyl-5'-Methylspiro[cyclohexane-1,2'-[3]oxa[1]azabicyclo[4.2.0]octane]-8'-one Following the procedures outlined in Examples 8–10 inclusive, the salt of (−)-(R)-3-amino-2-methyl propan-1-ol with (+)-N-(1-phenylethyl)-succinamic acid ($[\alpha]_D^{20} = +66.4°$) was elaborated to the title compound. The values obtained for the optical rotation of this compound was equal and opposite in sign to that quoted in Example 10.

We claim:

1. A process for the preparation of a compound of the formula (Ia) and/or (Ib):

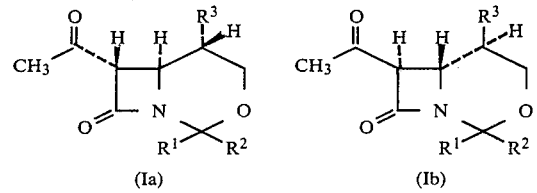

wherein $R^1$ and $R^2$ are independently hydrocarbon groups or are joined together so as to form a carbocyclic or heterocyclic ring, said hydrocarbon groups and said heterocyclic rings being unsubstituted or substituted by $C_{1-6}$ alkyl, hydroxy, bromine, chlorine, fluorine, carboxylic acid or salt or ester thereof, azido, tetrazolyl, alkanoyl, alkanoyloxy, aroyloxy, aroyl, aralkanoyloxy, aroxy, amino, protected amino, nitro, $C_{1-6}$ alkoxy, $C_{1-6}$ alkyl, aryl, $C_{1-6}$ alkylthio or arylthio, and $R^3$ is a hydrocarbon group unsubstituted or substituted by amino, mono, di- or trialkylamino, hydroxyl, alkoxyl, mercapto, alkylthio, arylthio, sulfamoyl, amidino, guanidino, nitro, chloro, bromo, fluoro, cyano or carboxy; which process comprises the ring-closing cyclization of a compound of the formula (II):

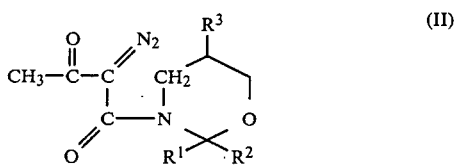

wherein R¹, R² and R³ are as defined in relation to formulae (Ia) and (Ib).

2. A process according to claim 1 wherein the compound of formula (II) is optically active.

3. A process according to claim 2 wherein the optically active compound of formula II produces a compound of formula (Ia) on cyclisation.

4. A process according to claim 1 wherein R³ is methyl.

5. A process according to claim 1 wherein the cyclisation is effected by means of a metal-catalysed intramolecular carbenoid insertion reaction.

6. A compound of formula II

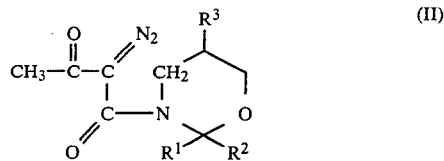

wherein R¹ and R² are independenly hydrocarbon groups or are joined together so as to form a carbocyclic or heterocyclic ring, said hydrocarbon groups and said heterocyclic rings being unsubstituted or substituted by $C_{1-6}$ alkyl, hydroxy, bromine, chlorine, fluorine, carboxylic acid or salt or ester thereof, azido, tetrazolyl, alkanoyl, alkanoyloxy, aroyloxy, aroyl, aralkanoyloxy, aroxy, amino, protected amino, nitro, $C_{1-6}$ alkoxy, $C_{1-6}$ alkyl, aryl, $C_{1-6}$ alkylthio or arylthio, and R³ is a hydrocarbon group unsubstituted or substituted by amino, mono-, di- or trialkylamino, hydroxyl, alkoxyl, mercapto, alkylthio, arylthio, sulfamoyl, amidino, guanidino, nitro, chloro, bromo, fluoro, cyano or carboxy.

7. A compound according to claim 6 in optically active form.

8. A compound according to claim 6 wherein R³ is methyl.

* * * * *